United States Patent
Chang et al.

[11] Patent Number: 6,037,513
[45] Date of Patent: Mar. 14, 2000

[54] HYDROALKYLATION OF AROMATIC HYDROCARBONS

[75] Inventors: Clarence D. Chang, Princeton; Jane C. Cheng, Voorhees, both of N.J.; Terry E. Helton, Glen Mills; Michael A. Steckel, Media, both of Pa.; Scott A. Stevenson, Houston, Tex.

[73] Assignee: Mobil Oil Corporation, Fairfax, Va.

[21] Appl. No.: 09/112,546

[22] Filed: Jul. 9, 1998

[51] Int. Cl.⁷ .............................. C07C 5/03; C07C 5/10; C07C 2/68; C07C 2/64; C07C 1/00

[52] U.S. Cl. ................ 585/467; 585/454; 585/455; 585/268; 585/269; 585/270

[58] Field of Search ................ 585/467, 454, 585/455, 268, 269, 270

[56] References Cited

U.S. PATENT DOCUMENTS

| | | | |
|---|---|---|---|
| 4,094,918 | 6/1978 | Murtha et al. | 260/668 R |
| 4,122,125 | 10/1978 | Murtha et al. | 260/688 R |
| 4,177,165 | 12/1979 | Murtha et al. | 252/455.2 |
| 4,206,082 | 6/1980 | Murtha et al. | 252/455 Z |
| 4,439,409 | 3/1984 | Puppe et al. | 423/328 |
| 4,826,667 | 5/1989 | Zones et al. | 423/277 |
| 4,954,325 | 9/1990 | Rubin et al. | 423/328 |
| 5,053,571 | 10/1991 | Makkee | 585/425 |
| 5,236,575 | 8/1993 | Bennett et al. | 208/46 |
| 5,250,277 | 10/1993 | Kresge et al. | 423/329.1 |
| 5,258,566 | 11/1993 | Kresge et al. | 585/467 |
| 5,362,697 | 11/1994 | Fung et al. | 502/71 |
| 5,488,194 | 1/1996 | Beck et al. | 585/475 |
| 5,557,024 | 9/1996 | Cheng et al. | 585/467 |

*Primary Examiner*—Walter D. Griffin
*Assistant Examiner*—Thuan D. Dang
*Attorney, Agent, or Firm*—Peter W. Roberts; Malcolm D. Keen

[57] ABSTRACT

There is described a process and a catalyst for the hydroalkylation of an aromatic hydrocarbon, particularly benzene, wherein the catalyst comprises a first metal having hydrogenation activity and a crystalline inorganic oxide material having a X-ray diffraction pattern including the following d-spacing maxima 12.4±0.25, 6.9±0.15, 3.57±0.07 and 3.42±0.07.

6 Claims, No Drawings

HYDROALKYLATION OF AROMATIC HYDROCARBONS

FIELD OF INVENTION

This invention relates to a catalyst and process for the hydroalkylation of aromatic hydrocarbons and particularly to a catalyst and process for the hydroalkylation of benzene to produce cyclohelbenzene.

BACKGROUND TO THE INVENTION

Cyclohexylbenzene can be used to produce phenol, which is one of the most important industrial chemicals in the world. As of December 1995, more than 88% of world phenol capacity was based on cumene peroxidation with acetone coproduction. One of the primary economic difficulties of the cumene peroxidation route is that it requires the existence of an available market for the co-produced acetone. Currently, the growth of market demand for phenol exceeds that for acetone, and hence there exists an acetone oversupply problem. It is expected that this unbalanced growth will continue for some time.

Hydroperoxidation of cyclohexylbenzene (analogous to cumene peroxidation) could offer an alternative route for phenol production without the problem of acetone co-production. This alternative route co-produces cyclohexanone, which is a much more valuable and desirable by-product than acetone. Thus, cyclohexanone is used partly for the manufacture of caprolactam and nylon, the same market that much phenol is intended for.

Dehydrogenation of cyclohexylbenzene also offers a low cost alternative to produce diphenyl from benzene. Diphenyl is used mainly for heat-transfer applications. Currently the main source of diphenyl is as a by-product (1 g diphenyl/100 g benzene) in benzene production by toluene dealkylation. The crude diphenyl is refined to 93–97% purity by distillation. High purity diphenyl can also be produced by direct thermal dehydrocondensation of benzene at 700–800° C. in gas or electrically heated tubular reactors. This process is energy intensive and produces by-products of terphenyl, higher polyphenyls and tars.

It is known that cyclohexylbenzene can be produced from benzene by the process of hydroalkylation or reductive alkylation. In this process, benzene is heated with hydrogen in the presence of a catalyst such that the benzene undergoes partial hydrogenation to produce cyclohexene which then alkylates the benzene starting material. Thus U.S. Pat. Nos. 4,094,918 and 4,177,165 disclose hydroalkylation of aromatic hydrocarbons over catalysts which comprise nickel- and rare earth-treated zeolites and a palladium promoter. Similarly, U.S. Pat. Nos. 4,122,125 and 4,206,082 disclose the use of ruthenium and nickel compounds supported on rare earth-treated zeolites as aromatic hydroalkylation catalysts. The zeolites employed in these prior art processes are zeolites X and Y. More recently, U.S. Pat. No. 5,053,571 has proposed the use of ruthenium and nickel supported on zeolite beta as an aromatic hydroalkylation catalyst. However, existing proposals for the hydroalkylation of benzene suffer from the problems that the selectivity to cyclohexylbenzene is low particularly at economically viable benzene conversion rates and that large quantities of unwanted by-products, particularly cyclohexane and methylcyclopentane, are produced.

An object of the present invention is to provide a process for the hydroalkylation of aromatic hydrocarbons with an improved selectivity for the desired cycloalkyl-substituted aromatic hydrocarbon, particularly cyclohexylbenzene, and decreased production of by-products such as cyclohexane and methylcyclopentane.

SUMMARY OF THE INVENTION

According to one aspect of the invention there is provided a process for the hydroalkylation of an aromatic hydrocarbon comprising the step of contacting the aromatic hydrocarbon with hydrogen in the presence of a dual-functional catalyst comprising a first metal having hydrogenation activity and a crystalline inorganic oxide material having a X-ray diffraction pattern including the d-spacing maxima at 12.4±0.25, 6.9±0.15, 3.57±0.07 and 3.42±0.07 Angstrom.

Preferably, the aromatic hydrocarbon is benzene.

Preferably, the crystalline inorganic oxide material is MCM-22.

Preferably, the first metal is selected from palladium, ruthenium, nickel and cobalt.

Preferably, the catalyst also contains a second metal, different from the first metal, and selected from zinc, tin, nickel and cobalt.

In a further aspect, the invention resides in a catalyst suitable for the hydroalkylation of an aromatic hydrocarbon comprising (a) a first metal having hydrogenation activity and selected from palladium, ruthenium, nickel and cobalt;

(b) a second metal, different from the first metal, and selected from zinc, tin, nickel and cobalt.; and (c) a crystalline inorganic oxide material having a X-ray diffraction pattern including d-spacing maxima at 12.4±0.25, 6.9±0.15, 3.57±0.07 and 3.42±0.07 Angstrom.

DETAILED DESCRIPTION OF THE INVENTION

This invention relates to a catalyst and process for the hydroalkylation of aromatic hydrocarbons, particularly benzene, to cycloalkylphenyl compounds, particularly cyclohexylbenzene, using as the catalyst a hydrogenation metal-containing crystalline inorganic oxide material having a X-ray diffraction pattern including d-spacing maxima at 12.4±0.25, 6.9±0.15, 3.57±0.07 and 3.42±0.07 Angstrom. The X-ray diffraction data used throughout this specification were obtained by standard techniques using the K-alpha doublet of copper as the incident radiation and a diffractometer equipped with a scintillation counter and associated computer as the collection system.

Suitable inorganic oxide materials are MCM-22 (described in U.S. Pat. No. 4,954,325), PSH-3 (described in U.S. Pat. No. 4,439,409), SSZ-25 (described in U.S. Pat. No. 4,826,667), MCM-36 (described in U.S. Pat. No. 5,250,277), MCM-49 (described in U.S. Pat. No. 5,236,575) and MCM-56 (described in U.S. Pat. No. 5,362,697), with MCM-22 being particularly preferred.

The hydrogenation metal is preferably selected from palladium, ruthenium, nickel, cobalt and mixtures thereof, with palladium and ruthenium being particularly preferred. In addition, the catalyst may contain a further hydrogenation metal, such as platinum, rhodium and rhenium, in addition to said preferred hydrogenation metals. The amount of hydrogenation metal present in the catalyst may vary significantly and will, for example, depend on the particular metal employed. Preferably, however, the amount of hydrogenation metal present is between 0.05 and 10 wt %, and more preferably between 0.1 and 5 wt %, of the catalyst.

The catalyst preferably contains a second metal component, in addition to and different from the hydrogenation metal, which acts to promote the hydrogenation function of the catalyst. Suitable second metal components are selected from zinc, tin, nickel, cobalt and mixtures thereof Again, the amount of second metal component present in the catalyst may vary significantly but preferably is between 0.05 and 10 wt %, and more preferably between 0.1 and 5 wt %, of the catalyst.

The catalyst of the invention may also include a matrix or binder which is composited with the inorganic oxide material. Such matrix materials include synthetic or naturally occurring substances as well as inorganic materials such as clay, silica and/or metal oxides. The latter may be either naturally occurring or in the form of gelatinous precipitates or gels including mixtures of silica and metal oxides. Naturally occurring clays which can be composited with the inorganic oxide material include those of the montmorillonite and kaolin families, which families include the subbentonites and the kaolins commonly known as Dixie, McNamee, Georgia and Florida clays or others in which the main mineral constituent is halloysite, kaolinite, dickite, nacrite or anauxite. Such clays can be used in the raw state as originally mined or initially subjected to calcination, acid treatment or chemical modification.

In addition to the foregoing materials, the inorganic oxide material employed herein may be composited with a porous matrix material, such as silica, alumina, zirconia, titania, silica-alumina, silica-magnesia, silica-zirconia, silica-thoria, silica-beryllia, silica-titania as well as ternary compositions such as silica-alumina-thoria, silica-alumina-zirconia, silica-alumina-magnesia and silica-magnesia-zirconia. The matrix can be in the form of a cogel. A mixture of these components could also be used.

The relative proportions of inorganic oxide material and binder may vary widely with the inorganic oxide material content ranging from about 1 to about 90 percent by weight and more usually in the range of about 30 to about 80 percent by weight of the composite The reaction conditions used in the process of the invention typically include a temperature of about 50 to 350° C., a pressure of about 100 to 7000 kPa, a benzene to hydrogen molar ratio of about 0.01 to 100 and a WHSV of about 0.01 to 100. In particular, it is important to keep the temperature as low as possible to minimize the formation of byproducts such as methylcyclopentane and methylcyclopentylbenzene. For this reason, the temperature is preferably maintained at or below about 150° C. and more preferably at or below about 120° C.

The products of the process of the invention will invariably include some dicycloalkylphenyl compounds which, where the aromatic feed is benzene, will be dicyclohexylbenzene (referred to as $C_{18}$ products in the Examples). Such dialkylated products can readily be separated from the effluent stream and converted to additional monoalkylated product by transalkylation with the aromatic feed, either by recycling the dialkylated product to the hydroalkylation reactor or by feeding the dialkylated product to separate transalkylation reactor. In the latter case, the transalkylation will preferably be effected in the presence of a catalyst containing the same crystalline inorganic oxide material as used in the hydroalkylation catalyst but in the absence of the metal components on the hydroalkylation catalyst and in the absence of a hydrogen co-feed.

The invention will now be more particularly described with reference to the accompanying Examples.

EXAMPLES 1–10

The following nine catalysts were prepared by impregnating MCM-22 extrudates (65 wt % MCM-22/35 wt % $Al_2O_3$ binder) with aqueous solutions of various metal salts using incipient wetness impregnation and then drying the resultant materials:

| Catalyst No. | Metal Content |
| --- | --- |
| 1 | 0.3 wt % Pd |
| 2 | 0.3 wt % Ru |
| 3 | 1.0 wt % Ni |
| 4 | 1.0 wt % Co |
| 5 | 0.6 wt % Pt |
| 6 | 0.3 wt % Rh |
| 7 | 0.6 wt % Re |
| 8 | 0.6 wt % Pt/0.6 wt % Sn |
| 9 | 0.3 wt % Ru/0.3 wt % Sn |
| 10 | 0.3 wt % Ru/0.3 wt % Zn |

A general procedure was then followed to test each metal-containing MCM-22 catalyst for benzene hydroalkylation. 2.0 g of the catalyst being tested was charged to a fixed-bed micro-reactor, where the catalyst was pretreated with 50 cc/min of flowing hydrogen for 2 hours at 300° C. and 1 atm pressure. After cooling the reactor to 120° C. in flowing hydrogen, benzene was fed into the reactor through a syringe pump at 60 cc/hour for 1 hr while the reactor pressure was increased to 150 psig. The benzene feed rate was then reduced to 2 WHSV and hydrogen/benzene ratio was adjusted to 1:1. Liquid products were collected in a cold product trap and analyzed off-line. The catalyst was then tested at 150° C. under otherwise identical conditions. Table 1 shows data obtained at 120° C., whereas Table 2 shows data obtained at 150° C.

TABLE 1

| Catalyst | 1 | 2 | 3 | 4 | 5 | 6 | 7 | 8 | 9 | 10 |
| --- | --- | --- | --- | --- | --- | --- | --- | --- | --- | --- |
| Days on stream | 1.9 | 1.8 | 1.1 | 0.8 | 1.1 | 0.8 | 0.8 | 0.9 | 9.0 | 3.8 |
| Benzene Conv, % | 23.8 | 47.9 | 6.7 | 8.8 | 31.0 | 33.7 | 0.7 | 34.1 | 37.7 | 43.1 |
| Selectivity, wt % | | | | | | | | | | |
| c-Hexane | 18.6 | 53.0 | 49.4 | 11.9 | 97.8 | 98.4 | — | 95.6 | 18.7 | 17.2 |
| c-Hexylbenzene | 73.8 | 41.7 | 50.2 | 80.4 | 2.1 | 1.6 | — | 4.4 | 67.3 | 67.6 |
| $C_{18}$ Products | 7.2 | 4.9 | 0.2 | 7.2 | 0.0 | 0.0 | — | 0.0 | 13.6 | 14.7 |
| Others | 0.4 | 0.4 | 0.2 | 0.5 | 0.1 | 0.0 | — | 0.0 | 0.4 | 0.5 |
| c-Hexylbenzene yield, wt % | 17.6 | 20 | 3.4 | 7.1 | 0.7 | 0.5 | — | 1.5 | 25.3 | 29.1 |

TABLE 2

| Catalyst | 1 | 2 | 3 | 4 | 5 | 6 | 7 | 8 |
|---|---|---|---|---|---|---|---|---|
| Days on stream | 7.9 | 4.8 | 4.9 | 5.8 | 3.0 | 3.1 | 2.1 | 3.8 |
| Benzene Conv, % | 48.6 | 59.8 | 9.7 | 9.8 | 34.0 | 33.9 | 0.0 | 42.0 |
| Selectivity, wt % | | | | | | | | |
| c-Hexane | 10.5 | 30.4 | 34.8 | 10.4 | 88.7 | 93.2 | — | 67.8 |
| c-Hexylbenzene | 70.3 | 58.5 | 60.1 | 78.5 | 10.9 | 6.7 | — | 29.5 |
| $C_{18}$ Products | 17.5 | 9.9 | 3.9 | 9.2 | 0.2 | 0.1 | — | 1.8 |
| Others | 1.7 | 1.2 | 1.2 | 1.9 | 0.2 | 0.0 | — | 0.9 |
| c-Hexylbenzene yield, wt % | 34.1 | 35 | 5.8 | 7.7 | 3.7 | 2.3 | — | 12.4 |

From Tables 1 and 2 it will be seen that MCM-22 catalysts with metals such as Pd, Ru, Ni, Co, Pt, Rh, Pt/Sn, Ru/Sn, and Ru/Zn were active at 120° C. and 150° C. for benzene hydroalkylation. Runs at 120° C. provided lower dialkylation $C_{18}$ products, whereas the runs at 150° C. provide higher benzene conversion. Among the metals utilized, Pd and Ru provided high activity for benzene conversion and high selectivity for cyclohexylbenzene. The use of second metal such as Sn improved catalyst activity and cyclohexylbenzene selectivity.

EXAMPLE 11

Catalyst No. 9, containing 0.3 wt % ruthenium and 0.3 wt % tin, was retested according to the general procedure described in Examples 1–10 but at a temperature of 120° C., a pressure of 110 psig and a WHSV of 1. After 22 days on stream, the benzene conversion was 43.9 wt % and the product selectivities were 12.8 wt % cyclohexane, 71.4 wt % cyclohexylbenzene, 15.2 wt % $C_{18}$ products and 0.6 wt % other products so that the cyclohexylbenzene yield was 31.4 wt %.

EXAMPLE 12

A further catalyst, containing 0.3 wt % ruthenium and 0.3 wt % tin on MCM-56 extrudates (65 wt % MCM-56/35 wt % $Al_2O_3$ binder), was prepared and tested according to the general procedure described in Examples 1–10 at a temperature of 120° C., a pressure of 150 psig and a WHSV of 2. After 3.8 days on stream, the benzene conversion was 51.0 wt % and the product selectivities were 45.0 wt % cyclohexane, 48.3 wt % cyclohexylbenzene, 6.1 wt % $C_{18}$ products and 0.6 wt % other products so that the cyclohexylbenzene yield was 24.6 wt %.

EXAMPLE 13 (Comparative)

A comparison catalyst containing 0.3 wt % ruthenium and 0.3 wt % tin on zeolite Beta extrudates (65 wt % zeolite Beta/35 wt % $Al_2O_3$ binder), was prepared and tested according to the general procedure described in Examples 1–10 at a temperature of 120° C., a pressure of 150 psig and a WHSV of 2. After 2 days on stream, the benzene conversion was 37.7 wt % and the product selectivities were 81.3 wt % cyclohexane, 15.2 wt % cyclohexylbenzene, 2.2 wt % $C_{18}$ products and 1.3 wt % other products so that the cyclohexylbenzene yield was only 5.7 wt %.

We claim:

1. A process for producing a cycloalkyl-substituted aromatic hydrocarbon comprising the step of contacting an aromatic hydrocarbon with hydrogen in the presence of a catalyst which has hydrogenation activity and alkylation activity and which comprises a first metal having hydrogenation activity and a crystalline inorganic oxide material having alkylation activity and an X-ray diffraction pattern including d-spacing maxima at 12.4±0.25, 6.9±0.15, 3.57±0.07 and 3.42±0.07 Angstrom.

2. The process of claim 1 wherein the crystalline inorganic oxide material is selected from the group consisting of MCM-22, PSH-3, SSZ-25, MCM-36, MCM-49 and MCM-56.

3. The process of claim 1 wherein the aromatic hydrocarbon is benzene.

4. The process of claim 1 wherein the first metal is selected from the group consisting of palladium, ruthenium, nickel and cobalt.

5. The process of claim 1 wherein the catalyst also contains a second metal, different from the first metal, and selected from the group consisting of zinc, tin, nickel and cobalt.

6. The process of claim 1 wherein the contacting step is conducted at a temperature of about 50 to 350° C., a pressure of about 100 to 7000 kPa, a benzene to hydrogen molar ratio of about 0.01 to 100 and a WHSV of about 0.01 to 100.

* * * * *